(12) United States Patent
Kirchhofer et al.

(10) Patent No.: US 6,277,101 B1
(45) Date of Patent: *Aug. 21, 2001

(54) INJECTION DEVICE

(75) Inventors: Fritz Kirchhofer, Sumiswald; Peter Michel, Burgdorf, both of (CH); Birger Hjertman, Vållingby (SE); Gustav Levander, Helsingborg (SE); Olle Ljungquist, Tåby (SE)

(73) Assignee: Disetronic Licensing AG, Burgdorf (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,553

(22) PCT Filed: Apr. 2, 1996

(86) PCT No.: PCT/CH96/00115

§ 371 Date: Jun. 18, 1998

§ 102(e) Date: Jun. 18, 1998

(87) PCT Pub. No.: WO97/36625

PCT Pub. Date: Oct. 9, 1997

(51) Int. Cl.[7] ................................................. A61M 5/00
(52) U.S. Cl. ............................ 604/232; 604/211; 604/208
(58) Field of Search .................................... 604/107, 131, 604/135, 207, 208, 209, 210, 211, 232, 218, 134; 222/309

(56) References Cited

U.S. PATENT DOCUMENTS

| | | |
|---|---|---|
| 4,592,745 | 6/1986 | Rex et al. . |
| 4,865,591 | 9/1989 | Sams . |
| 4,883,472 | 11/1989 | Michel . |
| 4,946,446 | 8/1990 | Vadher . |
| 4,973,318 | 11/1990 | Holm et al. . |
| 5,017,190 | 5/1991 | Simon et al. . |
| 5,084,060 | 1/1992 | Freund et al. . |
| 5,092,842 | 3/1992 | Bechtold et al. ............... 604/135 |
| 5,114,406 | 5/1992 | Gabriel et al. . |
| 5,273,544 | 12/1993 | Van de Wal . |
| 5,279,579 | 1/1994 | D'Amico . |
| 5,279,585 | 1/1994 | Balkwill . |

(List continued on next page.)

FOREIGN PATENT DOCUMENTS

| | | |
|---|---|---|
| 3638984 | 11/1986 | (DE) . |
| 3645245 | 11/1986 | (DE) . |
| 3900926 | 7/1989 | (DE) . |
| 4223958 | 7/1992 | (DE) . |
| 4112259 | 10/1992 | (DE) . |
| 0037696 | 3/1981 | (EP) . |
| 0058536 | 8/1982 | (EP) . |
| 0245312 | 10/1986 | (EP) . |
| 0268191 | 11/1987 | (EP) . |
| 0298067 | 6/1988 | (EP) . |
| B327910 | 1/1989 | (EP) . |
| 0373321 | 10/1989 | (EP) . |

(List continued on next page.)

*Primary Examiner*—Anhtuan T. Nguyen
*Assistant Examiner*—Jeremy Thissell
(74) *Attorney, Agent, or Firm*—Dorsey & Whitney LLP

(57) ABSTRACT

An injection device for injecting a preselectable dose of a liquid substance from an ampoule (2) with a stopper (12) located in an ampoule-holder (1) has a sleeve-shaped mechanism holder (3) mechanically linked to the stopper (12) and containing a sliding rod (4) which acts on the ampoule (2). The sliding rod (4) is surrounded by a sliding sleeve (5) mechanically coupled to the ampoule (2) and closed at its upper end by a lid (7). A dosing sleeve (13) is provided with a stepped member (13) arranged at the upper end of the mechanism holder (3) to preselect the dose of liquid substance to be injected. The dose to be administered can be adjusted by turning the dosing sleeve (6) provided with the stepped member (13).

11 Claims, 2 Drawing Sheets

U.S. PATENT DOCUMENTS

| | | | |
|---|---|---|---|
| 5,279,586 | 1/1994 | Balkwill | 604/207 |
| 5,292,314 | 3/1994 | D'Alessio et al. | |
| 5,295,976 | 3/1994 | Harris . | |
| 5,320,609 | 6/1994 | Haber et al. | |
| 5,336,183 | 8/1994 | Greelis et al. | |
| 5,337,311 | 8/1994 | Mahukar . | |
| 5,370,629 | 12/1994 | Michel et al. | |
| 5,472,430 | 12/1995 | Vaillancourt et al. | |
| 5,496,293 | 3/1996 | Huggenberger . | |
| 5,514,097 | 5/1996 | Knauer . | |
| 5,527,294 | 6/1996 | Weatherford et al. | |
| 5,549,558 | 8/1996 | Martin . | |
| 5,549,575 | 8/1996 | Giambattista et al. | |
| 5,573,510 | 11/1996 | Isaacson . | |
| 5,582,598 * | 12/1996 | Chanoch | 604/208 |
| 5,591,136 | 1/1997 | Gabriel . | |
| 5,591,138 | 1/1997 | Vaillancourt . | |
| 5,593,390 | 1/1997 | Castellano et al. | |
| 5,609,577 | 3/1997 | Haber et al. | |
| 5,643,214 | 7/1997 | Marshall et al. | |
| 5,658,259 | 8/1997 | Pearson et al. | |
| 5,674,204 * | 10/1997 | Chanoch | 604/211 |
| 5,679,111 | 10/1997 | Hjertman et al. | |
| 5,725,508 | 3/1998 | Chanoch et al. | |
| 5,728,074 | 3/1998 | Castellano et al. | |
| 5,743,889 | 4/1998 | Sams . | |
| 5,807,346 | 9/1998 | Frezza . | |

FOREIGN PATENT DOCUMENTS

| | | |
|---|---|---|
| 496141 | 1/1991 | (EP) . |
| 0516473 | 5/1992 | (EP) . |
| 0498737 | 8/1992 | (EP) . |
| 0554995 | 8/1993 | (EP) . |
| 0338806 | 2/1994 | (EP) . |
| 0594349 | 4/1994 | (EP) . |
| 0627229 | 5/1994 | (EP) . |
| 2701211 | 2/1993 | (FR) . |
| WO 8702895 | 5/1987 | (WO) . |
| WO8808725 | 11/1988 | (WO) . |
| WO 9110460 | 7/1991 | (WO) . |
| WO 9305835 | 8/1992 | (WO) . |
| WO 9218179 | 10/1992 | (WO) . |
| WO 9316740 | 9/1993 | (WO) . |
| WO 9409841 | 5/1994 | (WO) . |
| WO 9415120 | 7/1994 | (WO) . |
| 9504563 | 8/1994 | (WO) . |
| WO 9501812 | 1/1995 | (WO) . |
| WO 9607443 | 3/1996 | (WO) . |

* cited by examiner section A-A

INJECTION DEVICE

RELATED APPLICATIONS

This application claims the priority of PCT application no. PCT/CH96/00115, filed Apr. 2, 1996, which is incorporated herein by reference.

BACKGROUND OF THE INVENTION

1. Field of the Invention

The invention relates to an injection device for injecting a selectable dose of a liquid substance from an ampoule located in an ampoule holder, comprising a sleeve-shaped mechanism holder mechanically coupled thereto, in the interior of the mechanism holder a longitudinally shiftable shaft with a piston disposed thereon being provided which acts on the ampoule, wherein the shaft being surrounded by an also longitudinally shiftable advancing sleeve, mechanically coupled thereto, which in its upper end area is closed by a lid.

2. Description of the Prior Art

Such an injection device is known from EP 0 373 321 B 1 that consists of an ampoule sleeve for receiving the ampoule and a delivering mechanism. In turn, this is composed of a cylindrical piston shaft with an inner hollow cylinder and an outer hollow cylinder which is formed in one piece with this and which exhibits a guiding cam on its outer shell. A dosing ring is fixed radially to the outer hollow cylinder. The dosing can be read off by means of a scaling fastened to the outer perimeter of the dosing ring through a sight glass set into the housing of the mechanism holder. The delivering mechanism is disposed longitudinally movably in the mechanism holder by means of a retaining spring and secured by a lid screwable into the housing of the mechanism holder. The dosing ring rests against the lid with the force of the retaining spring. The housing of the mechanism holder is provided on its inside with elongated slots of different length in which the corresponding guiding cam of the delivering mechanism is able to glide. As a result, the lift of the delivering mechanism is determined by the length of the elongated slot cooperating with the guiding cam. The adaptation of the dose to be administered to the needs of a patient takes place exclusively by an authorized person, e.g. a physician. A special-purpose wrench is necessary, by means of which an interlocking ring of the device can be unlocked until the guiding cam of the delivering mechanism is released from the respective elongated slot. The physician is then able to select the desired dose by rotation of the released delivering mechanism and renewed catch of the guiding cam into a corresponding elongated slot.

Once selected, the dose cannot be varied without considerable effort. In addition, based on the construction of the delivering mechanism, the injection device can only be used for delivering a single dose although possibly a sufficient supply of medicine is still available in the ampoule. In order to administer another dose of medicine, the ampoule sleeve must be unlocked from the mechanism holder and disposed of together with the ampoule possibly still containing medicine.

An injection device of generic type is known from EP 0 037 596 B 1 with which a dose of a liquid substance to be administered can be taken from an ampoule via a transmission mechanism of tractive force acting in one direction upon operating a locking cap. The transmission mechanism of tractive force consists in that one pushing part is equipped with a plurality of teeth and the other pushing part with a pawl, which intermesh and therefore effect the advance of the transmission mechanism of tractive force only in one direction of ejection of the dose to be administered. The maximum lift height and therefore the maximum dose to be administered is limited via a notch and a stop. The operator of the injection device is also able to select less than the maximum dose by listening to the number of clicks which occur when, during the advance, the teeth of the pushing part catch in the pawl. In this connection, one click corresponds to the minimum dose. The operating element, the locking cap, is pushed back up to a stop by means of a spring.

This injection device is designed for extremely careful operation since a click can easily be overheard and different doses to be administered not be securely adjusted. In addition, no display unit is foreseen for the dose to be selected.

SUMMARY OF THE INVENTION

The present invention is therefore based on the problem to identify an injection device of the type described above which is simple in the constructive design and simple in the handling and with which the operator himself by simple movements is safely able to select the dose to be administered.

This problem is thereby solved in that a dosing sleeve with a stepped member is provided for selecting a dose of a liquid substance to be injected, which is disposed on the mechanism holder in its upper end area, wherein the dose to be respectively administered being adjustable by a rotation of the dosing sleeve with the stepped member.

In this case, the dosing sleeve is composed of an operating element with a profile, an adjoining cylinder with dose imprint, a catch stop, and the stepped member adjoining this. The constructive coupling of the dosing sleeve to the injection device is thereby characterized in that together with the stepped member and the cylinder with the dose imprint it surrounds the advancing sleeve.

The injection device according to the invention has the fundamental advantage that a dose, adjusted once, can be applied repeatedly; the user just has to load the injection device before each injection. The selection of the dose to be applied is quite easy due to a simple rotation of the dosing sleeve.

Further advantageous embodiments of the invention can be taken from the dependent claims.

One embodiment of the invention is represented in the figures.

BRIEF DESCRIPTION OF THE DRAWINGS

It is shown in.

DESCRIPTION OF THE PREFERRED EMBODIMENTS

Figure 1:
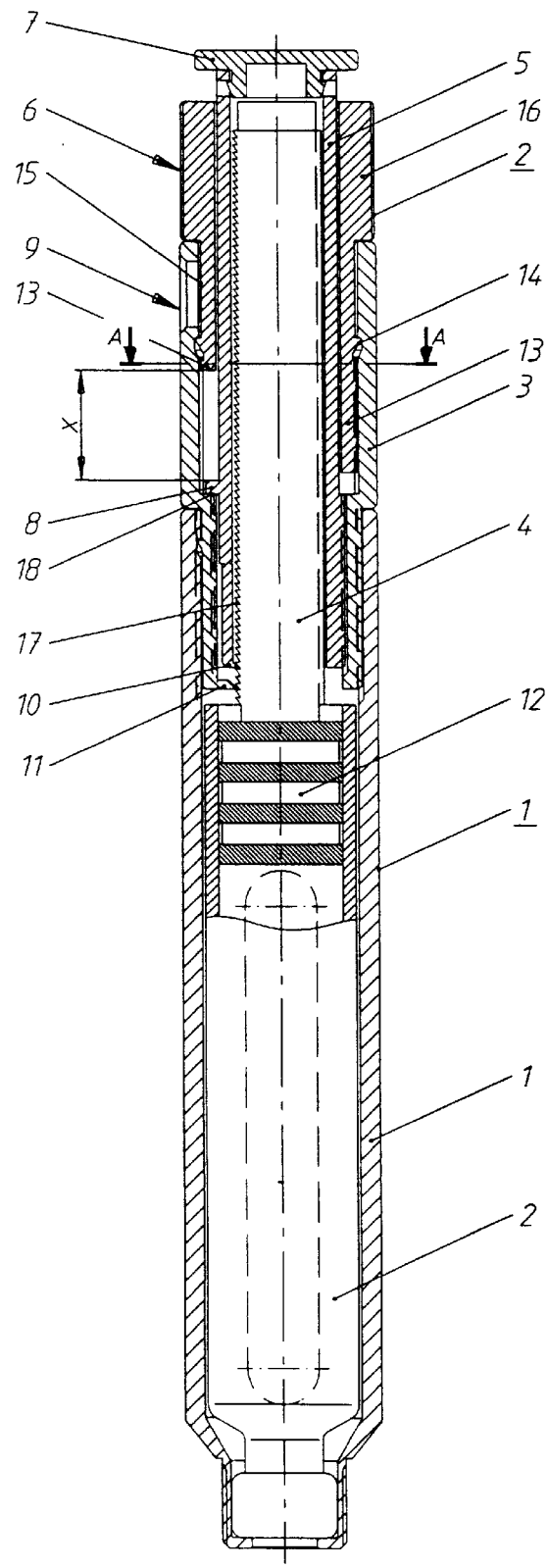
FIG. 1: the injection device according to the invention in section.
Figure 2:
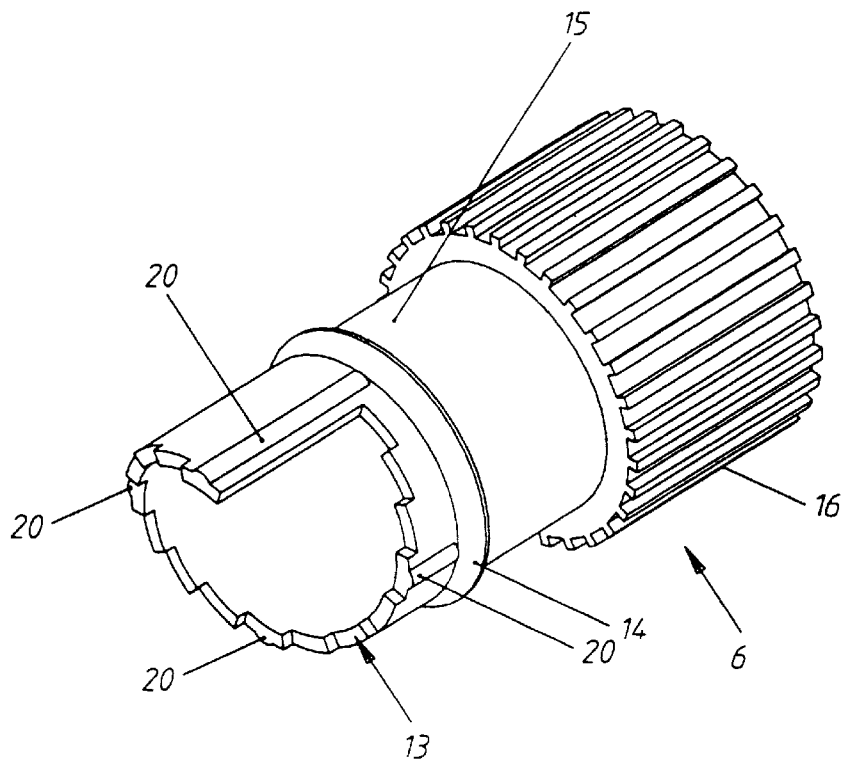
FIG. 2: the dosing sleeve with stepped member in a perspective view.

The injection device shown in FIG. 1 consists of the ampoule holder 1 in which the ampoule 2 with the piston 12 and with the liquid substance to be administered are located. The sleeve-shaped mechanism holder 3 is mechanically coupled to the ampoule holder 1 by a thread or another suitable lock such as a bayonet lock. In the interior of the mechanism holder 3, the longitudinally shiftable shaft 4 is disposed acting on the piston 12 of the ampoule 2. The shaft 4 is surrounded by the also longitudinally shiftable advancing sleeve 5 mechanically coupled thereto, which is closed in its upper end area by the lid 7. For selecting a dose of the liquid substance to be injected, the dosing sleeve 6 with the stepped member 13 is provided which is arranged on the mechanism holder 3 in its upper end area. In this case, the dosing sleeve 6 with the stepped member 13 surrounds the advancing sleeve 5. The dose to be respectively adjusted and to be administered is selectable by a simple rotation of the dosing sleeve 6 with the stepped member 13. The dosing sleeve 6 is mechanically coupled to the mechanism holder 3 via the catch stop 14. The dosing sleeve 6 consists, according to FIG. 2, of the profiled operating element 16, the adjoining cylinder 15 with the dose imprint, the catch stop 14, and the stepped member 13 adjoining this. The cam 8 is disposed on the advancing sleeve 5, which upon withdrawing the advancing sleeve 5 in the direction of the lid 7 comes to a stop against the step of the stepped member 13 respectively adjusted. Upon pressing down the advancing sleeve 5, the cam 8 comes to a stop against the shoulder 18 of the mechanism holder 3, resulting in the injection lift X.

Figure 3:
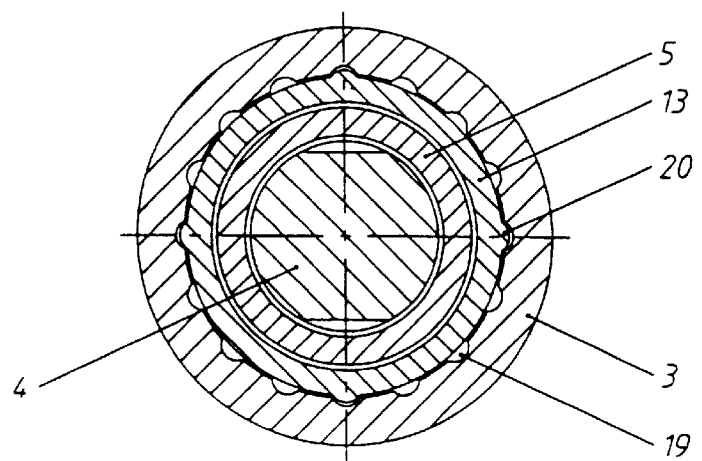
FIG. 3: a section along the line A—A in FIG. 1.

For mechanical coupling of shaft 4 with the advancing sleeve 5 the shaft 4 is provided with the toothing 17 which cooperates with the locking cam 10 of the advancing sleeve 5. In this case, the depth of tooth of the toothings 17 on the shaft 4 corresponds to the step height of the stepped member 13. In the area of its lower end, the mechanism holder 3 comprises the catch 11 which also cooperates with the toothing 17 of the shaft 4. The dose imprint on the cylinder 15 is visible via a window 9 in the mechanism holder 3. In its interior, the mechanism holder 3 comprises a plurality of bulges 19 into which the projections 20 of the stepped member 13 catch. (FIG. 3) The shaft 4 is non-rotatably longitudinally shiftable.

The mode of operation of the injection device according to the invention is as follows:

The operator turns the dosing sleeve 6 with the stepped member 13 until the desired dose imprint on the cylinder appears in the window 9. Then, the injection device is loaded. FIG. 1 shows this before the loading. For the loading, the advancing sleeve 5 is pulled upward by the lid 7, mechanically coupled thereto, until the cam 8 which is part of the advancing sleeve 5 comes to a stop against the currently adjusted step of the stepped member 13. In this case, the locking cam 10 of the advancing sleeve 5 glides over the toothing 17 of the shaft 4, the teeth of which (not shown) are arrow-shaped downward. In order to prevent that the shaft 4 is nevertheless shifted upward at the same time, the catch 11 is provided on the mechanism holder 3 which is not shiftable longitudinally. Thus, the catch 11 braces itself into the toothing 17 and prevents motion of the shaft 4 upward. For administering the selected dose, pressure in the downward direction is exerted by the operator on the lid 7 and on the advancing sleeve 5 coupled thereto. In this case, the locking cam 10 braces itself into the toothing 17 and, so to say, takes the shaft 4 along and the piston 12 coupled to the shaft 4 exerts pressure on the ampoule 2 located in the ampoule holder 1, with which the liquid substance is applied by administering it through an injection needle (not shown). Upon pressing down the advancing sleeve 5 by means of the lid 7, the teeth of the toothing 17 also glide over the catch 11 of the mechanism holder 3, wherein the catch 11 is out of mesh by means of the selected arrow-shape of the teeth of the toothing 17. The advance motion of the advancing sleeve 5 in the downward direction lasts until the cam 8 comes to a stop against the shoulder 18 of the mechanism holder 3 so that the selected dose of the liquid substance is administered. The injection device is prepared by renewed loading for one or more subsequent injections. The shaft 4 remains during the loading processes in the immediately before-given state by means of the toothing of catch 11 with the teeth of toothing 17. In particular, the shaft moves only in one direction, that is so to say downward, while the advancing sleeve lets itself move in two directions, so to say upward for loading and downward for applying. The injection device according to the invention can serve for the administering of medicine. However, it is also possible to administer lotions and other liquid substances with it.

The length of the injection lift X is determined by the individual differences of the steps of the stepped member 13 such that with an ampoule 2 with a specific diameter X is an integral multitude of a dose unit.

What is claimed is:

1. An injection device for injecting a selectable dose of a substance, the injection device comprising:
   a longitudinally shiftable shaft;
   an advancing sleeve surrounding the shaft, wherein the advancing sleeve is sidably connected to the shaft to permit the shaft to move in one direction relative to the advancing sleeve; and
   a dosing sleeve partially surrounding the advancing sleeve, the dosing sleeve having radially dispersed steps each having a longitudinal length,
   wherein rotation of the dosing sleeve selects the dose by selecting one of the radially dispersed steps.

2. The injection device of claim 1 wherein rotation of the dosing sleeve sets the dose by defining a stroke distance of the shaft corresponding to the longitudinal length of the step selected.

3. The injection device of claim 1 wherein subsequent equivalent doses may be administered without adjustment of the dosing sleeve.

4. The injection device of claim 1 wherein the advancing sleeve contains a lid for advancement or retraction by a user.

5. The injection device of claim 1, wherein the advancing sleeve contains a stop and a locking cam and the shaft contains notches, wherein the locking cam mates with the notches of the shaft, and wherein the stop defines the stroke distance of the shaft between one step of the dosing sleeve and a shoulder of the injection device.

6. The injection device of claim 5 wherein each step of the dosing sleeve has a different length.

7. The injection device of claim 5 further comprising a mechanism holder which is attachable to an ampoule holder containing an ampoule, wherein the mechanism holder contains a catch which cooperates with the notches of the shaft.

8. The injection device of claim 7 wherein the dosing sleeve comprises an operating element having a profile, a cylinder with a dose imprint, a catch stop and a stepped portion adjoining thereto, and wherein the stepped portion contains projections.

9. The injection device of claim 8 wherein the dose imprint on the cylinder is visible through a window in the mechanism holder.

10. The injection device of claim 8 wherein the mechanism holder contains a plurality of bulges, and wherein the projections of the stepped portion catch in the bulges of the mechanism holder.

11. An injection device for injecting a selectable dose of a liquid substance from an ampoule, the injection device comprising:

a longitudinally shiftable shaft having teeth thereon, the shaft being operably coupled to the ampoule;

an advancing sleeve attached to a lid and surrounding the shaft, the advancing sleeve having a stop and a locking cam, wherein the locking cam mates with the teeth of the shaft to permit the shaft to move in one direction relative to the advancing sleeve;

a mechanism holder connected to an ampoule holder containing the ampoule, wherein the mechanism holder surrounds the advancing sleeve, and wherein the mechanism holder contains a shoulder and a catch which cooperates with the teeth of the shaft; and a dosing sleeve surrounding the advancing sleeve and having radially dispersed steps each having a longitudinal length, wherein rotation of the dosing sleeve sets the dose by defining a stroke length of the stop between one step of the dosing sleeve and the shoulder of the mechanism holder, the stroke length being equivalent to the longitudinal length of the step selected, and wherein subsequent equivalent doses may be administered by pushing and pulling the lid without further adjustment of the dosing sleeve.

* * * * *

UNITED STATES PATENT AND TRADEMARK OFFICE
CERTIFICATE OF CORRECTION

PATENT NO.     : 6,277,101 B1                                              Page 1 of 1
DATED          : August 21, 2001
INVENTOR(S)    : Fritz Kirchhofer et al.

It is certified that error appears in the above-identified patent and that said Letters Patent is hereby corrected as shown below:

Column 1,
Line 62, please delete "EPO 037596B1" and insert -- EPO 037696B1 -- therefor.

Signed and Sealed this

Twenty-fifth Day of June, 2002

*Attest:*

*Attesting Officer*

JAMES E. ROGAN
*Director of the United States Patent and Trademark Office*